United States Patent [19]

Matsunaga et al.

[11] Patent Number: 5,654,190

[45] Date of Patent: Aug. 5, 1997

[54] PROCESS FOR PRODUCING PLANT BELONGING TO THE SECTION LEUCE

[75] Inventors: Etsuko Matsunaga; Ayako Todate; Hiroyasu Ebinuma, all of Tokyo, Japan

[73] Assignee: Nippon Paper Industries Co., Ltd., Tokyo, Japan

[21] Appl. No.: 443,161

[22] Filed: May 17, 1995

[30] Foreign Application Priority Data

May 18, 1994 [JP] Japan ................................. 6-103749

[51] Int. Cl.$^6$ ................................................ C12N 5/00
[52] U.S. Cl. ........................ 435/430; 435/430.1; 800/200
[58] Field of Search ........................ 435/240.49, 240.48, 435/240.4, 240.45, 420, 430, 431; 800/200

[56] References Cited

PUBLICATIONS

Yamanouchi et al. *J. Seric Sci Jpn* 62(2). 1993 pp. 145–151.

Ahuja. *Silvae Genetics* 32(3–4) 1983 pp. 131–135.

"Propagation and Breeding of Arboreous Plant", Nogyo Toshio, pp. 248–256, 1989.

Plant Cell Reports, vol. 9, pp. 165–167, 1990, Gary D. Coleman, et al., "Axillary Shoot Proliferation and Growth of Populus Deltoides Shoot Cultures".

Plant Cell, Tissue and Organ Culture, vol. 36, pp. 59–71, 1994, Glenn T. Howe, et al., "Agrobacterium–Mediated Transformation of Hybrid Poplar Suspension Cultures and Regeneration of of Transformed Plants".

Plant Cell Reports, vol. 11, pp. 137–141, 1992, Jean Charles Leple, et al., "Transgenic Poplars: Expression of Chimeric Genes Using Four Different Constructs".

Can. J. For. Res., vol. 21, pp. 1321–1328, 1991, Ned B. Klopfenstein, et al., "Transgenic Populus Hybrid Expresses a Wound–Inducible Potato Proteinase Inhibitor II–Cat Gene Fusion".

Plant Physiol., vol. 93, pp. 1110–1116, 1990, Marc De Block, "Factors Influencing the Tissue Culture and the Agrobacterium Tumefaciens–Mediated Transformation of Hybrid Aspen and Poplar Clones".

Plant Cell Reports, vol. 5, pp. 464–467, 1986, Eun–Woon Noh, et al., "High Efficiency Shoot Regeneration from Callus of Quaking Aspen (Populous Tremuloides Michx.)".

J. Jpn. for. Soc., vol. 50(9), pp. 267–273, 1968, Takayama, "Studies on the Breeding of Aspens (I) Height Growth in the Early Stage of F1 Seedlings of Populous Sieboldii MIQ.xP. Grandidentata Michx." (with partial English translation).

Mol Gen Genet, vol. 206, pp. 192–199, 1987, JoAnne J. Fillatti, et al., "Agrobacterium Mediat Transformation and Regeneration of Populous".

*Primary Examiner*—Blaine Lankford
*Attorney, Agent, or Firm*—Oblon, Spivak, McClelland, Maier & Neustadt, P.C.

[57] ABSTRACT

A process for producing a plant is described, which comprises the step of culturing a tissue of a plant belonging to the genus Populus, the section Leuce, thereby regenerating the plant via an adventitious bud, wherein the adventitious bud is differentiated from the cultured tissue using an adventitious bud differentiation medium having nitrogen source concentrations of from 1 to 15 mM as ammonia-nitrogen and from 15 to 50 mM as nitrate-nitrogen.

14 Claims, No Drawings

PROCESS FOR PRODUCING PLANT BELONGING TO THE SECTION LEUCE

FIELD OF THE INVENTION

The present invention relates to process for producing a plant, which comprises culturing a tissue of a plant belonging to the section Leuce of the genus Populus, thereby regenerating the plant via an adventitious bud.

BACKGROUND OF THE INVENTION

Several tree species belonging to the genus Populus are cultured mainly in the temperate regions of the northern hemisphere, because they grow quickly and find versatile use in applications such as afforestation trees and pulp wood. In general, these species are proliferated with asexual propagation using cuttings. Species belonging to the section Leuce which are applicable to forestation in Japan, as hard woods (broad leaf trees) for pulp use, are propagated by a root laying method because of their low rooting frequency by cuttings. However, since their large scale propagation by this method requires a prolonged period of time and a large nursery area, many studies have been made on their large scale propagation by a tissue culture to resolve these problems.

The tissue culture is a technique in which a part of plants is aseptically cultured under appropriate conditions to propagate and/or regenerate it into a mature plant. Since plants can be regenerated from a part of plant tissues within a marked short period of time by applying this technique, its applications to the large scale propagation of plantlets are expected. For example, there is a known process in which an anther or a stem of a species belonging to the section Leuce is cultured to induce growth of a callus as a dedifferentiated tissue from which plants are regenerated through differentiation of shoots (*Propagation and Breeding of Arboreous Plant*, Nogyo Tosho, pp. 248–256, 1989). However, since cali (calluses) are apt to cause genetic mutation during their growth, mutants are probably generated at the stage of callus growth even by using this method. This mutation becomes a problem when clone plantlets having the same genetic constitution are produced. Also, although this method has a shorter propagating period than the root laying method, the culturing must be completed through steps of inducing a callus from an explant such as an anther and a stem, growing the callus and differentiating shoots therefrom, and so several months are still required to cover the period from the beginning of the culturing of the explant to the completion of the differentiation of shoots. In consequence, it is also important to shorten this period when plantlets are produced in a large scale for industrial purpose, or selection and propagation of superior individuals are repeated for breeding. Application of the method to the creation of an alien gene-transformed hybrid aspen (*Populus sieboldii×Populus grandidentata*) has been reported (Matsunaga et al., Abstract of Papers, Second Tree Molecular Biology Symposium, pp. 72–77, 1992). However, because of the above-described reasons, this method still has practical problems such as low efficiency in obtaining clone plantlets having a desired gene introduced therein and prolonged period of time until completion of the regeneration of a plant.

In order to resolve these problems, an another tissue culture method is carried out in which plants are regenerated from a tissue thereof by differentiating adventitious buds without employing a step for inducing and growing a callus. The term "adventitious bud" as used herein means a bud induced by a certain means from a tissue which should not become a bud by nature, and a plant can be regenerated therefrom by culturing it under appropriate conditions similar to the differentiation of shoots from a callus. In this method, the differentiation of adventitious buds are induced under such conditions that a callus is not induced or allowed to grow if induced, so that the adventitious buds are differentiated from a shoot used as the material directly or from a slightly grown callus. In consequence, this method is relatively free from the problem of causing genetic mutation during the culturing step and requires only a shorter period of time for regenerating a plant than the redifferentiation method which always requires steps for the inducing and growing a callus and redifferentiating shoots from the callus. This method is, therefore, useful for the above-described industrial and breeding purposes and is now frequently used as a means for efficiently obtaining a transformed plant in which a gene is introduced by using an agrobacterium method.

In using a tissue culture technique, it is necessary to select a plant tissue to be cultured, a medium composition to be used in the culturing and other conditions such as temperature and light, depending on the purpose of the culturing. However, combinations of these conditions and the results obtained thereby do not always show a certain relationship, and it is rather common that the same result is not obtained when different species or even different varieties of the plant are used as the materials, respectively. For example, according to a report regarding detailed examination of the effects of plant hormone compositions in a culture medium and plant varieties (genotypes) on the differentiation of adventitious buds, the adventitious bud differentiation ratio varies within the range of from 0 to 100% depending on the difference in varieties even when the same basal medium supplemented with the same kind and amount of a plant hormone is used (Coleman et al., *Plant Cell Reports*, vol. 9, pp. 165–167, 1989). In consequence, the most important subject to be solved when a plant tissue culture technique is used is to find the optimum culture conditions depending on each plant to be used as the material and each purpose of the culturing. However, studies on their propagation by the tissue culture technique in the field of arboreous plants are slower in progress than those of herbaceous plants such as vegetables, flowers and ornamental plants. Accordingly, even when the adventitious bud differentiation is studied on arboreous plants, the current studies are limited to model studies in which the conditions used for the adventitious bud differentiation of the tobacco plant, which belongs to the herbaceous plant, are used as such merely changing the plant hormone composition in the medium, and a variety that can induce differentiation of adventitious buds relatively easily under such conditions is used as the material. For example, regeneration of a plant by adventitious bud differentiation from a leaf of a plant belonging to the genus Populus has been reported (Fillatti et al., *Molecular General Genetics*, vol. 206, pp. 192–199, 1987). However, a surprisingly limited amount of information exists on the studies of culture conditions including medium compositions which were conducted to induce efficient adventitious bud differentiation in practically useful arboreous plants.

SUMMARY OF THE INVENTION

An object of the present invention is, therefore, to provide a process for the short time and large scale production of plants having the same genetic constitution, in which a plant belonging to the section Leuce which, among species belonging to the genus Populus, is useful in forestation as a hard wood pulp tree is used as the material, and an adventitious bud is efficiently induced from a tissue of the plant directly or from a callus slightly grown from the tissue and regenerated into a plant.

To resolve the above-described problems involved in the prior art, the present inventors have conducted intensive studies and found as the result that, in a plant belonging to the section Leuce, differentiation of an adventitious bud can be induced efficiently from a tissue of the plant while hardly causing callus growth, by culturing the tissue using a medium having a specified composition of the nitrogen source.

Thus, this and other objects of the present invention have been attained by a process for producing a plant, which comprises the step of culturing a tissue of a plant belonging to the genus Populus, the section Leuce, thereby regenerating the plant via an adventitious bud, wherein the adventitious bud is differentiated from the cultured tissue using an adventitious bud differentiation medium having nitrogen source concentrations of from 1 to 15 mM as ammonia-nitrogen and from 15 to 50 mM as nitrate-nitrogen.

DETAILED DESCRIPTION OF THE INVENTION

In the present invention, the medium for the adventitious bud differentiation has nitrogen source concentrations of from 1 to 15 mM as ammonia-nitrogen and from 15 to 50 mM as nitrate-nitrogen, preferably from 5 to 10 mM as ammonia-nitrogen and from 30 to 40 mM as nitrate-nitrogen. The concentrations of the ammonia-nitrogen and nitrate-nitrogen outside these ranges exert bad influence on the adventitious bud differentiation. For high efficiency induction of the differentiation of adventitious buds, it is preferable to adjust a molar ratio of the ammonia-nitrogen to the nitrate-nitrogen to from 1:2 to 1:5, particularly 1:3. For example, these nitrogen source concentrations are adjusted by adding $NH_4NO_3$ or $KNO_3$ to the medium.

Compositions known such as MS (Murashige-Skoog) medium, LS (Linsmaier-Skoog) medium, and WP (Woody Plant) medium can be used be side the nitrogen source. Furthermore, cytokinin compounds such as benzyladenine (BA), kinetin, zeatin, 2-isopentenyladenine and thidiazuron may be added as a plant hormone to enhance the differentiation and growth of adventitious buds. These plant hormones may be used alone or as a mixture of two or more. The amount thereof which should be added depends on the activity of each cytokinin used, but is generally within the range of from 0.05 to 5 mg/l. On the other hand, auxins are not particularly required but may be added within such a range that they do not inhibit redifferentiation of stems and leaves. Also, for the differentiation and growth of adventitious buds, they are preferably cultured at a temperature of from 15° to 30° C. and under at least 10 hours a day of illumination at 500 luxes or more.

The adventitious bud differentiation medium according to the present invention can be applied to plants belonging the section Leuce of the genus Populus and shows particularly excellent effects on the differentiation of adventitious buds of a hybrid aspen of *Populus sieboldii* and *Populus grandidentata*. The hybrid aspen has been obtained by cutting branches from 5 selected female *Populus sieboldii* wild trees found in a mountainous region of Tamayama-mura, Iwate-gun, Iwate Prefecture, Japan, culturing the cut branches in water for blooming, crossing the resulting flowers with pollen of a selected male tree of Canadian *Populus grandidentata* to produce about 30,000 seeds, obtaining 1,200 healthy seedlings from the seeds and selecting F1 individuals showing most active growth (cultivated in an experimental forest owned by Akita Jujo Chemicals Co., Ltd.). It has been reported that these hybrids are particularly more excellent in their growth than other species belonging to the section Leuce or interspecific hybrids thereof and express a significant heterosis (Takayama, *J. Jpn. For. Soc.*, vol. 50(9), pp. 267–273, 1968).

In the present invention, any one of the stem, terminal bud, lateral bud, shoot apex and petiole of a plant can be used as the tissue to be cultured. The term "terminal bud" as used herein means a bud formed on the tip of a stem; the term "lateral bud" means a bud formed on the side of a stem; and the term "shoot apex" means a part which contains a meristematic tissue existing in the stem end, such as the tip part of these buds. These tissues are excised from the plant, sterilized in the usual way, washed with sterile water and then cultured using the above-described adventitious bud differentiation medium immediately or after an appropriate preculture treatment, thereby differentiating adventitious buds. The sterilization step is not required when a plant aseptically grown in a flask is used as the material. When the tissues are precultured, the medium for the preculture is not particularly limited, but it is preferable to shorten the preculture period when growth of a callus is found during the preculturing.

When the adventitious bud is differentiated and grown into a length of 1 to 3 cm, it is excised from the cultured tissue and transplanted into a rooting medium for rooting and subsequently a complete plant is regenerated. Commonly known medium such as the above-described MS, LS and WP mediums may be used as the rooting medium. The medium may be diluted by a factor of about ⅓. The rooting medium may have the same nitrogen source composition as the medium for the adventitious bud differentiation according to the present invention. Plant hormones may not be added, but auxins may be added alone up to a concentration of 0.5 mg/l. If the concentration is more than 0.5 mg/l, it is not preferred because of a strong tendency to induce callus formation from the transplanted tissue. Particularly, it is preferable to add IBA (indolebutyric acid) alone at a concentration of from 0.01 to 0.2 mg/l. Cytokinins should not be added because of their tendency to inhibit rooting, but may be added if their concentration is ⅒ or less of the concentration of auxins.

Either a liquid culture or a solid culture can be used as the culturing system of the present invention. However, the solid culture is preferred for healthy growth of adventitious buds and differentiation and growth of roots. In a solid culture, a medium solidification agent such as agar and gellan gum may be used. In an agar medium, the agar is added to the medium at a concentration of from 0.7 to 1.0 w/v %, or in a gellan gum medium, the gellan gum is added to the medium at a concentration of from 0.2 to 0.3 w/v %, each based on the medium volume. Then, they are dissolved and solidified in the usual way.

In the present invention, the differentiation of adventitious bud can be induced efficiently from a tissue of a plant belonging to the section Leuce of the genus Populus, hardly causing callus growth, when the tissue is cultured using a known medium used in the tissue culture of arboreous plants by merely changing its original nitrogen source concentration to from 1 to 15 mM as ammonia-nitrogen and to from 15 to 50 mM as nitrate-nitrogen.

Although the mechanism of the differentiation induction is not clear yet, plant cells are originally possessed of a totipotent differentiation potency, namely a potency to regenerate one plant from one somatic cell. In consequence, a plant cell changes its physiological state when put under appropriate conditions and differentiates various tissues depending on the changed state. Probably, in the plant belonging to the section Leuce, both concentrations of two nitrogen sources, namely ammonia-nitrogen and nitrate-nitrogen, are deeply related to a process which triggers a physiological state that induces differentiation of adventitious bud, so that physiological state of its cells changes and differentiation of adventitious bud is induced when concentrations of nitrogen sources in a tissue culture medium are adjusted to the ranges according to the present invention.

The present invention is now illustrated in greater detail by way of the following examples, but it should be understood that the present invention is not to be construed as being limited thereto.

EXAMPLES

Example 1

Under aseptic conditions, a stem of an aseptically flask-grown plantlet of a hybrid aspen Y63 (collected at an experimental forest owned by Akita Jujo Chemical Co., Ltd.) was cut in an internode piece of 5 mm in length, further cut in half longitudinally and then inoculated into MS agar solid medium (sucrose 2 w/v %, zeatin 0.5 mg/l, agar 0.8 w/v %) whose nitrogen sources have been changed to 10-mM ammonia-nitrogen and 30-mM nitrate-nitrogen. After cultured for 1 month at a temperature of 25° C. under an illuminance of 3,000 luxes (the whole day), differentiation of adventitious buds was found in 23 of the 24 inoculated tissues. The shoot grown from each bud became a length of 2 to 3 cm after about 1 month of additional culturing under the same conditions, and then was aseptically cut off and inoculated into the same medium, except that zeatin was replaced by 0.05 mg/l of IBA for rooting. After 1 month of the inoculation, 61 young plantlets were obtained.

Comparative Example 1

Stems of an aseptically flask-grown plantlet of the hybrid aspen Y63 were cultured in the same manner as in Example 1, except that the normal MS medium was used as the adventitious bud differentiation medium. Differentiation of adventitious buds was found in 2 of the 24 inoculated tissues, and 2 young plantlets were obtained.

Example 2

Stems of an aseptically flask-grown plantlet of the hybrid aspen Y63 were cultured in the same manner as in Example 1, except that the concentrations of ammonia-nitrogen and nitrate-nitrogen of the adventitious bud differentiation medium were changed to 5 mM and 20 mM, respectively. Differentiation of adventitious buds was found in 12 of the 24 inoculated tissues, and 16 young plantlets were obtained.

Example 3

Stems of an aseptically flask-grown plantlet of the hybrid aspen Y63 were cultured in the same manner as in Example 1, except that the concentrations of ammonia-nitrogen and nitrate-nitrogen of the adventitious bud differentiation medium were changed to 10 mM and 40 mM, respectively. Differentiation of adventitious buds was found in 15 of the 24 inoculated tissues, and 41 young plantlets were obtained.

Comparative Example 2

Stems of an aseptically flask-grown plantlet of the hybrid aspen Y63 were cultured in the same manner as in Example 1, except that the concentrations of ammonia-nitrogen and nitrate-nitrogen of the adventitious bud differentiation medium were changed to 5 mM and 10 mM, respectively. Differentiation of adventitious buds was found in 5 of the 24 inoculated tissues, and 7 young plantlets were obtained.

Comparative Example 3

Stems of an aseptically flask-grown plantlet of the hybrid aspen Y63 were cultured in the same manner as in Example 1, except that the concentrations of ammonia-nitrogen and nitrate-nitrogen of the adventitious bud differentiation medium were changed to 20 mM and 20 mM, respectively. Differentiation of adventitious buds was found in 3 of the 24 inoculated tissues, and 5 young plantlets were obtained.

Example 4

A stem of a hybrid aspen Y78 (collected at an experimental forest owned by Akita Jujo Chemical Co., Ltd.) grown in a constant temperature room at 25° C. under an illuminance of 3,000 luxes (the whole day) was cut in an internode piece and sterilized by stirring it for 10 minutes in a sodium hypochlorite solution having an available chlorine concentration of 1%. Under aseptic conditions, this stem was washed with sterile water, cut in a length of 5 mm, further cut in half longitudinally and then inoculated into WP agar solid medium (sucrose 2 w/v %, zeatin 0.5 mg/l, agar 0.8 w/v %) whose nitrogen sources have been changed to 10 mM ammonia-nitrogen and 30 mM nitrate-nitrogen. After cultured in the same manner as in Example 1, differentiation of adventitious buds was found in 8 of the 10 inoculated tissues, and 16 young plantlets were obtained.

Comparative Example 4

Stems of the hybrid aspen Y78 were cultured in the same manner as in Example 4, except that the normal WP medium was used as the adventitious bud differentiation medium. Differentiation of adventitious buds was found in 2 of the 10 inoculated tissues, and 3 young plantlets were obtained.

Example 5

A pre-sprouting branch of a hybrid aspen Y79 (collected at an experimental forest owned by Akita Jujo Chemical Co., Ltd.) grown in the field was thoroughly washed and allowed to sprout by culturing it in water in a constant temperature room at 25° C. under an illuminance of 3,000 luxes (the whole day). A node containing a lateral bud portion was cut off and sterilized by stirring it for 10 minutes in a sodium hypochlorite solution having an available chlorine concentration of 1%. Under aseptic conditions, this nod portion was washed with sterile water and cultured using the same adventitious bud differentiation medium and culture conditions as in Example 1. After 2 months, differentiation of adventitious buds was observed and 1 to 5 shoots were developed from these buds per 1 inoculated tissue. Next, these shoots were aseptically cut off, inoculated into 2/3 dilution MS gellan gum solid medium (sucrose 2 w/v %, IBA 0.05 mg/l, gellan gum 0.3 w/v %) and then the rooting culture was continued to obtain young plantlets.

Since these young plantlets were obtained by aseptic culturing in flask, their habituation to external environment was carried out by washing roots of each young plantlet which was grown into about 5 cm, transplanting the plantlet into a polyethylene pot filled with Metro-mix 350

(manufactured by W. R. Grace Co., Ltd.) which has been sterilized using an autoclave, covering the pot with a vinyl bag and then cultivating it at 25° C. under an illuminance of 3,000 luxes. The cover was removed 2 weeks thereafter and the cultivation was continued. After 3 months of the habituation, the young plantlets grew into about 30 cm.

Results of the above examples are shown in Table 1 below, and compositions of the MS and WP media used herein as the basal media are shown in Table 2 below.

TABLE 1

Effects of ammonia-nitrogen and nitrate-nitrogen on adventitious bud differentiation

|  | Example | | | | | Comparative Example | | | |
|---|---|---|---|---|---|---|---|---|---|
|  | 1 | 2 | 3 | 4 | 5 | 1 | 2 | 3 | 4 |
| Hybrid aspen type | Y63 stem | Y63 stem | Y63 stem | Y78 stem | Y79 lateral bud | Y63 stem | Y63 stem | Y63 stem | Y78 stem |
| Adventitious bud differentiation medium*[1] | | | | | | | | | |
| Basal medium | MS | MS | MS | WP | MS | MS | MS | MS | WP |
| $NH_4^+$-N (mM)*[2] | 10 | 5 | 10 | 10 | 10 | 21 | 5 | 20 | 5 |
| $NO_3^-$-N (mM)*[3] | 30 | 20 | 40 | 30 | 30 | 39 | 10 | 20 | 10 |
| Tissues inoculated | 24 | 24 | 24 | 10 | — | 24 | 24 | 24 | 10 |
| Differentiation ratio (*)*[4] | 96 | 50 | 63 | 80 | — | '8 | 21 | 13 | 20 |
| Young plant regenerated | 61 | 16 | 41 | 16 | — | 2 | 7 | 5 | 3 |

*[1] It includes other components below: 2 w/v % sucrose, 0.5 mg/l zeatin, 0.8 w/v % agar;
*[2] ammonia-nitrogen;
*[3] nitrate-nitrogen;
*[4] number of adventitious bud-differentiated tissues/number of inoculated tissues × 100

TABLE 2

| Basal medium composition (mg/l) | | |
|---|---|---|
| Component | MS medium | WP medium |
| $NH_4NO_3$ | 1,650 | 400 |
| $KNO_3$ | 1,900 | 0 |
| $K_2SO_4$ | 0 | 990 |
| $CaCl_2.2H_2O$ | 440 | 96 |
| $Ca(NO_3)_2.4H_2O$ | 0 | 556 |
| $MgSO_4.7H_2O$ | 370 | 370 |
| $KH_2PO_4$ | 170 | 170 |
| $FeSO_4.7H_2O$ | 27.8 | 27.8 |
| $Na_2$-EDTA | 37.3 | 37.3 |
| $MnSO_4.4H_2O$ | 22.3 | 22.3 |
| $ZnSO_4.7H_2O$ | 8.6 | 8.6 |
| $CoCl_2.6H_2O$ | 0.025 | 0 |
| $CuSO_4.5H_2O$ | 0.025 | 0.25 |
| $Na_2MoO_4.2H_2O$ | 0.25 | 0.25 |
| KI | 0.83 | 0 |
| $H_3BO_3$ | 6.2 | 6.2 |
| Nicotinic acid | 0.5 | 0.5 |
| Pyridoxine hydrochloride | 0.5 | 0.5 |
| Thiamin hydrochloride | 0.1 | 1.0 |
| myo-Inositol | 100 | 100 |
| L-Glycine | 2 | 2 |

When the medium nitrogen concentration was within the range of from 1 to 15 mM as ammonia-nitrogen and from 15 to 50 mM as nitrate-nitrogen, the adventitious bud differentiation ratio was 50% or more independent of the basal media. However, the adventitious bud differentiation ratio rapidly decreased when either one of the two nitrogen sources was outside the above range. In addition, the adventitious bud differentiation ratio was particularly high when the molar ratio of ammonia-nitrogen to nitrate-nitrogen was 1:3. Further, when the concentrations of ammonia-nitrogen and nitrate-nitrogen in the adventitious bud differentiation medium were within the above-described range, a large number of young plantlets regenerated from these adventitious buds were obtained, even though it varied depending on growing conditions such as rooting and habituation after their differentiation.

Thus, according to the present invention, differentiation of adventitious buds can be induced efficiently from tissues of a plant belonging to the section Leuce of the genus Populus directly or via a slight callus growth, and plants can be regenerated therefrom, thus rendering possible short time and large scale production of plants having the same genetic constitution.

Also, according to the present invention, known media in the tissue culture of arboreous plants can be used by merely adjusting concentrations of ammonia-nitrogen and nitrate-nitrogen to specified ranges, respectively.

Due to the effects of the present invention, not only industrial large scale production of plantlets of a plant belonging to the section Leuce, but also large scale propagation of the plantlets for use in the selection of individuals having excellent characters and large scale propagation of the selected individuals or other individuals in which useful genes are introduced can be carried out efficiently within a short period of time by using the tissue culture method.

While the invention has been described in detail and with reference to specific embodiments thereof, it will be apparent to one skilled in the art that various changes and modifications can be made therein without departing from the spirit and scope thereof.

What is claimed is:

1. A process for producing a hybrid aspen, Populus sieboldii×Populus grandidentata, which comprises culturing a tissue of said hybrid aspen in an adventitious bud differentiation medium effective for producing said hybrid aspen, and having nitrogen source concentrations of from 1 to 15 mM as ammonium ion and from 15 to 50 mM as nitrate ion, thereby regenerating the hybrid aspen via an adventitious bud, and wherein a molar ratio of the ammonia-nitrogen to the nitrate-nitrogen in the adventitious bud differentiation medium is from about 1:2 to 1:5.

2. The process as claimed in claim 1, wherein the tissue of said plant which is cultured is a tissue selected from a stem, a shoot apex, a terminal bud, a lateral bud and a petiole of the plant.

3. The process as claimed in claim 2, wherein said stem is of hydrid aspen Y63.

4. The process as claimed in claim 2, wherein said stem is of hybrid aspen Y78.

5. The process as claimed in claim 2, wherein said lateral bud is of hydrid aspen Y79.

6. The process as claimed in claim 1, wherein the adventitious bud differentiation medium is Murashige-Skoog medium of which ammonia-nitrogen concentration and nitrate-nitrogen concentration as nitrogen sources are modified to from 1 to 15 mM and from 15 to 50 mM, respectively.

7. The process as claimed in claim 1, wherein the adventitious bud differentiation medium is Woody Plant medium of which ammonia-nitrogen concentration and nitrate-nitrogen concentration as nitrogen sources are modified to from 1 to 15 mM and from 15 to 50 mM, respectively.

8. The process as claimed in claim 1, wherein the adventitious bad differentiation medium contains from 5 to 10 mM of ammonia-nitrogen and from 30 to 40 mM of nitrate-nitrogen as nitrogen sources.

9. The process as claimed in claim 1, wherein a molar ratio of the ammonia-nitrogen to the nitrate-nitrogen in the adventitious bud differentiation medium is 1:3.

10. The process as claimed in claim 1, wherein said ammonium ion is present at concentration of from 5 to 10 mM, and said nitrate ion is present at concentration of from 30 to 40 mM.

11. The process as claimed in claim 1, wherein said adventitious bud differentiation medium comprises a plant hormone to enhance the differentiation in growth of adventitious buds selected from the group consisting of benzyladenine, kinetin, zeatin, 2-isopentenyladenine and thidiazuron.

12. The process as claimed in claim 11, wherein said plant hormone is added in the amount of from 0.05 to 5 mg/l.

13. The process as claimed in claim 1, wherein said tissue is cultured at a temperature of from 15° to 30° C. and under at least 10 hours a day of illumination at 500 luxes or more.

14. The process as claimed in claim 1, wherein said medium is a liquid or solid medium.

* * * * *